(12) United States Patent
Shimamoto et al.

(10) Patent No.: US 9,445,605 B2
(45) Date of Patent: Sep. 20, 2016

(54) METHOD FOR DISINFECTION OR INFECTION CONTROL AGAINST A NON-ENVELOPED VIRUS

(71) Applicants: Hiroshima University, Higashi-Hiroshima-shi, Hiroshima (JP); Altan Co., Ltd., Ota-ku, Tokyo (JP)

(72) Inventors: Tadashi Shimamoto, Higashi-Hiroshima (JP); Yasushi Okinaka, Higashi-Hiroshima (JP); Takemasa Sakaguchi, Hiroshima (JP); Toru Tsuji, Tokyo (JP); Yoshiaki Nakai, Tokyo (JP)

(73) Assignees: Hiroshima University, Hiroshima (JP); Altan Co., Ltd., Tokyo (JP)

(*) Notice: Subject to any disclaimer, the term of this patent is extended or adjusted under 35 U.S.C. 154(b) by 138 days.

(21) Appl. No.: 13/939,692

(22) Filed: Jul. 11, 2013

(65) Prior Publication Data

US 2013/0302453 A1 Nov. 14, 2013

Related U.S. Application Data

(62) Division of application No. 12/935,473, filed as application No. PCT/JP2009/056635 on Mar. 31, 2006, now abandoned.

(30) Foreign Application Priority Data

Mar. 31, 2008 (JP) ................. 2008-091602
Aug. 5, 2008 (JP) ................. 2008-201841

(51) Int. Cl.
*A61K 36/44* (2006.01)
*A61K 36/00* (2006.01)
(Continued)

(52) U.S. Cl.
CPC ............ *A01N 65/08* (2013.01); *A61K 31/05* (2013.01); *A61K 31/19* (2013.01); *A61K 31/194* (2013.01);
(Continued)

(58) Field of Classification Search
None
See application file for complete search history.

(56) References Cited

U.S. PATENT DOCUMENTS 3,891,781 A 6/1975 Bauer et al.
5,043,160 A * 8/1991 Wursch ............... A23C 9/1546
424/757

(Continued)

FOREIGN PATENT DOCUMENTS

GB 2432528 A 5/2007
JP 54014515 A 2/1979
(Continued)

OTHER PUBLICATIONS

Kantoch et al. The Action of Tannin on the Process and Components of Phagocytosis. II. Studies with viruses. Arch Immunol Et Therap Exptl, (1962) vol. 10, No. 1, pp. 66-76 (Abstract only provided).*
(Continued)

*Primary Examiner* — Patricia A Leith
(74) *Attorney, Agent, or Firm* — The Webb Law Firm (57) ABSTRACT

Provided herein is a method for disinfection or infection control against a non-enveloped virus using a composition including, as an active ingredient, a persimmon extract containing tannin from an astringent fruit of a plant of the genus *Diospyros*, such as the plant *Diospyros kaki*. The non-enveloped virus is a non-enveloped virus belonging to the genus Betanodavirus, Aquavirnavirus, Ranavirus, Enterovirus, Mastadenovirus, Vesivirus, or Rotavirus. In certain embodiments, the persimmon extract is prepared by heating a squeezed juice or an extract from an astringent fruit of a plant of the genus *Diospyros*, or obtained by treating a squeezed juice or an extract from an astringent fruit of the plant of the genus *Diospyros* with an alcohol, in order to inactivate an enzyme contained therein. The persimmon extract may also contain at least condensed tannin.

8 Claims, 4 Drawing Sheets

(51) Int. Cl.
  *A01N 65/08* (2009.01)
  *A61K 31/05* (2006.01)
  *A61K 31/19* (2006.01)
  *A61K 31/194* (2006.01)
  *A61K 31/235* (2006.01)
  *A61K 31/353* (2006.01)
  *A61K 31/60* (2006.01)
  *A61K 31/7024* (2006.01)
  *A61K 36/74* (2006.01)
  *A61K 45/06* (2006.01)

(52) U.S. Cl.
  CPC ........... *A61K 31/235* (2013.01); *A61K 31/353* (2013.01); *A61K 31/60* (2013.01); *A61K 31/7024* (2013.01); *A61K 36/44* (2013.01); *A61K 36/74* (2013.01); *A61K 45/06* (2013.01)

(56) References Cited

U.S. PATENT DOCUMENTS

| | | | |
|---|---|---|---|
| 5,043,357 A | 8/1991 | Hoffler et al. | |
| 5,491,068 A | 2/1996 | Benjamin et al. | |
| 6,083,518 A | 7/2000 | Lindahl | |
| 6,139,842 A * | 10/2000 | Matsuda | A23L 1/222 424/47 |
| 6,641,827 B2 * | 11/2003 | Yoshida | A01N 65/00 424/405 |
| 7,972,635 B2 | 7/2011 | Seabrook, Jr. et al. | |
| 2003/0180395 A1 * | 9/2003 | Bueter | 424/725 |
| 2005/0180930 A1 | 8/2005 | Abiru et al. | |
| 2005/0186172 A1 * | 8/2005 | Courtin | A61K 8/97 424/74 |
| 2006/0278086 A1 | 12/2006 | Inagaki et al. | |
| 2007/0003492 A1 | 1/2007 | Kitahata et al. | |
| 2009/0047305 A1 * | 2/2009 | Tanaka | A61K 8/498 424/195.17 |
| 2010/0240600 A1 | 9/2010 | Shimamoto et al. | |
| 2013/0095171 A1 * | 4/2013 | Tsai | A61K 36/076 424/450 |
| 2013/0302453 A1 * | 11/2013 | Shimamoto | A01N 65/08 424/771 |

FOREIGN PATENT DOCUMENTS

| | | | |
|---|---|---|---|
| JP | 59128329 A | | 7/1984 |
| JP | 361170374 A | * | 8/1986 |
| JP | 362265959 A | * | 11/1987 |
| JP | 63014702 A | | 1/1988 |
| JP | 1265023 A | | 10/1989 |
| JP | 402203776 A | * | 8/1990 |
| JP | 9059151 A | | 3/1997 |
| JP | 2004065174 A | | 3/2004 |
| JP | 02004065174 A | * | 3/2004 |
| JP | 2004331641 A | | 11/2004 |
| JP | 2004345971 A | | 12/2004 |
| JP | 2005232043 A | | 9/2005 |
| JP | 2006206558 A | | 8/2006 |
| JP | 2006306836 A | | 11/2006 |
| JP | 2007044007 A | * | 2/2007 |
| JP | 2008063332 A | * | 3/2008 |
| KR | 2003024111 | * | 3/2003 |
| KR | 758236 B1 | | 9/2007 |
| KR | 20070002466 B1 | | 9/2007 |
| WO | 2007128191 A1 | | 11/2007 |
| WO | 2008153077 A1 | | 12/2008 |

OTHER PUBLICATIONS

MacPhillamy: Drugs From Plants; Plant Science Bulletin, Botanical Society of America, vol. 9, No. 2, Apr. 1963.*
Medscape Online, COXSACKIEVIRUSES Clinical Presentation; Online, URL<http://emedicine.medscape.com/article/215241-clinical> 4 pages, Oct. 23, 2014.*
Phillipson, J. New Drugs From Nature—It Could Be Yew; Phytotherapy Research 13 (1999) pp. 2-8.*
Raskin et al. Can an Apple a Day Keep the Doctor Away? Current Pharmaceutical Design, Oct. 2004, 3419-3429.*
Revilla et al. Comparison of Several Procedures Used for the Extraction of Anthocynains From Red Grapes; J. Agric. Food Chem. 1998, 46, pp. 4592-4597.*
Smet et al. Herbal Remedies; The New England Journal of Medicine; Dec. 19, 2002, vol. 347, Issue 25, p. 2046, 11 pages.*
Wang Recent Advances in Extraction of Nutraceuticals From Plants; Trends in Food Science & Technology 17 (2006) 300-312.*
Zhong et al. Antiviral Activity of Arbidol Against Coxsackie Virus B5 In Vitro and In Vivo; Arch Virol (2009) 154: 601-607.*
Sanchez-Vega et al. Enzyme Inactivation on Apple Juice Treated by Ultrapasteurization and Pulsed Electric Fields Technology; Journal of Food Processing and Preservation, 33 (2009) 486-499.*
Matsuo, Tomoaki et al., "Comparative Studies of Condensed Tannins from Several Young Fruits", J. Japan. Soc. Hort. Sci. (1981), vol. 50, No. 2, pp. 262-269.
Matsuo, Tomoaki et al., "A Simple and Rapid Purification Method of Condensed Tannins from Several Young Fruits", Agric. Biol. Cem. (1981), vol. 45, No. 8, pp. 1885-1887.
Sugiyama, Hiroshi et al., "Studies on anti-norovirus action of plant derived components and development of novel ethanol preparation thereof", Jap. Society of Food Microbiology Gakujutsu Sokai Koen Yoshishu (2007), vol. 28, p. 56.
The Yomiuri Shimbun, "Persimmon Juice Inhibits Norovirus Traced by Hiroshima University Associate Professor et al. (Hiroshima)", The Yomiuri Shimbun (Jan. 16, 2008) Osaka Chokan, p. 33.
Mukoyama, Atsushi et al., "Inhibition of Rotavirus and Enterovirus Infections by Tea Extracts", Jpn. J. Med. Sci. Biol. (1991), vol. 44, pp. 181-186.
Poschetto, Lorenza Ferrero et al., "Comparison of the Sensitivities of Noroviruses and Feline Calicivirus to Chemical Disinfection under Field-Like Conditions", Applied and Environmental Microbiology (Sep. 2007), vol. 73, No. 17, pp. 5494-5500.
Koslov, M.V. et al., "Hepatitis C Virus RNA-Dependent RNA Polymerase: Study on the Inhibition Mechanism by Pyrogallol Derivatives", Biochemistry (Moscow) (2006), vol. 71, No. 9, pp. 1021-1026.
Carson, R. S. et al., "The Inactivation of Influenza Viruses by Tannic Acid and Related Compounds", J. Bacteriol. (1953), vol. 66, No. 5, pp. 572-575.
Kadoi, Takahiro et al., "Antivirus Effect of Persimmon Juice Against Non-enveloped Viruses", The Japanese Society of Virology Gakujutsu Shukai Program (Oct. 1, 2008), vol. 56, p. 344.
Calobonga.com; Online: URL<http://www.calobonga.com/calorieCounter/food/9263/0/calorie-counter.lz> 2 pages, accessed on Feb. 8, 2013.

* cited by examiner

METHOD FOR DISINFECTION OR INFECTION CONTROL AGAINST A NON-ENVELOPED VIRUS

CROSS-REFERENCES TO RELATED APPLICATIONS

This application is a division of co-pending U.S. patent application Ser. No. 12/935,473 filed Mar. 31, 2009, which claims priority of Japanese Patent Application No. 2008-091602, filed on Mar. 31, 2008, and Japanese Patent Application No. 2008-201841, filed on Aug. 5, 2008, all of which are incorporated herein by reference in their entireties.

BACKGROUND OF THE INVENTION

1. Technical Field

The present invention relates to an antiviral agent that has an excellent effect on non-enveloped viruses (e.g., fish disease viruses such as viral nervous necrosis virus (NNV), aquavirnavirus (ABV) and red seabream iridovius (RSIV); feline calicivirus which is an infectious pathogen of cats; human pathogenic viruses such as Coxsackie virus and adenovirus), that is highly safe for the human body, and that contains as an active ingredient at least one selected from the group consisting of extracts of plants of the genus *Diospyros* containing tannin, catechins, wattle tannin, pentagalloyl glucose, coffee tannin, alkyl gallates, pyrogallol, organic acids and/or salts thereof, and also relates to an antiviral composition containing the antiviral agent and useful for disinfection and infection control against the viruses.

2. Background Art

In general, viral diseases are difficult to cure because antibiotics have no effect thereon and thus become a major problem for humans and animals such as domestic animals. It is still fresh in our minds that SARS and avian influenza have recently attracted interest, and viral diseases also become a major problem for cultured fishes. However, there is no effective curing method for non-enveloped viruses, while surfactants and alcohols are effective for enveloped viruses, and a main measure against the non-enveloped viruses is prevention by vaccines.

"The astringent juice of the persimmon" produced by fermenting an extract from a persimmon has been used as Chinese herbal medicine, such as an antihypertensive agent, in China for a long time and is also familiar to Japanese as folk medicine. The astringent juice of the persimmon is rich in tannin and is believed to have astringency (the property of contracting a tissue by combining to a protein or another substance), antimicrobial action, and deodorizing action. The structure and a purification method of tannin (condensed tannin) contained in *Diospyros kaki* can be found in the following two papers (Matsuo and Itoo, 1981a/1981b: Non-patent Literatures 1 and 2).

As a composition containing the astringent juice of the persimmon or tannin of persimmon, for example, there has been proposed an antimicrobial dental composition (JP 2005-232043 A: Patent Literature 1) prepared by covering an extract from the astringent juice of the persimmon with cyclodextrin to further improve handleability and antimicrobial properties, and an anticancer agent and an antipneumonic viral agent (JP 2004-331641A: Patent Literature 2) prepared by adding and mixing the astringent juice of the persimmon with a component such as a peptide polysaccharide contained in Reishi spore.

JP 2006-206558 A (Patent Literature 3) discloses an antimicrobial composition containing a tannin substance, a fatty acid ester, and a chelating agent (Claim 1). Examples of the tannin substance include tannic acid, pyrocatechin, gallic acid, persimmon tannin, tea tannin, and gall tannin (Claim 4). However, the efficacy of the antimicrobial composition is demonstrated only for tannic acid in *Escherichia coli* and *Staphylococcus aureus* (Examples), and Patent Literature 3 does not specifically disclose a technical idea that persimmon tannin among the tannin substances has marked antiviral properties for non-enveloped viruses and thus persimmon tannin is very important as a component of an antiviral composition.

JP 2006-306836 A (Patent Literature 4) discloses that specified phenol derivatives are effective as inactivators for various viruses and also discloses various gallates as the phenol derivatives. However, Patent Literature 4 does not disclose viruses of the genera Vesivirus and Rotavirus and only n-octyl gallate is used in examples.

In addition, the inventors have proposed an anti-norovirus agent for norovirus that causes food poisoning and infectious gastroenteritis, the agent using a persimmon extract, and an anti-norovirus composition containing the anti-norovirus agent (International Publication No. 08/153077 pamphlet: Patent Literature 5).

Patent Literature 1: JP 2005-232043 A
Patent Literature 2: JP 2004-331641A
Patent Literature 3: JP 2006-206558 A
Patent Literature 4: JP 2006-306836 A
Patent Literature 5: International Publication No. 08/153077 pamphlet
Non-patent Literature 1: MATSUO, Tomoaki and ITOO, Saburo (1981a): Comparative Studies of Condensed Tannins from Several Young Fruits. J. Japan. Soc. Hort. Sci., 50(2), 262-269.
Non-patent Literature 2: MATSUO, Tomoaki and ITOO, Saburo (1981b): A Simple and Rapid Purification Method of Condensed Tannins from Several Young Fruits. Agric. Biol. Chem., 45(8), 1885-1887.

It is an object of the present invention to provide an antiviral agent that has an excellent inactivating action on non-enveloped viruses and that is highly safe for the human body, and an antiviral composition containing the antiviral agent and useful for disinfection for the viruses and prevention of infection of the viruses.

SUMMARY OF THE INVENTION

To solve the problems described above, the present inventors searched substances and plant components approved as food or food additives, that is, materials safe to eat, for a substance having an antiviral activity, and completed the present invention by finding that an extract from a plant of the genus *Diospyros* containing tannin has marked antiviral activity for a wide range of non-enveloped viruses and that other tannin substances or tannin-like substances have antiviral activity for non-enveloped viruses.

The gist of the present invention is as follows.

[1] An antiviral agent against an non-enveloped virus comprising, as an active ingredient, at least one selected from the group consisting of an extract of a plant of the genus *Diospyros* containing tannin (hereinafter referred to as a "persimmon extract"), a catechin, wattle tannin, pentagalloyl glucose, coffee tannin, an alkyl gallate (excluding that in the persimmon extract i.e., wherein the alkyl gallate is not endogenous to the persimmon extract), pyrogallol, an organic acid and/or a salt thereof (excluding that in the persimmon extract), the antiviral agent satisfying at least one selected from the group consisting of the following requirements [a], [b], [c], [d], and [e]:

[a] A persimmon extract is used as the active ingredient for non-enveloped viruses other than viruses of the genera Mastadenovirus, Vesivirus, Rotavirus, Betanodavirus, Aquavirnavirus, and Ranavirus.

[b] When the non-enveloped virus is a virus of the genus Mastadenovirus, at least one selected the group consisting of a persimmon extract, a catechin, and wattle tannin is used as the active ingredient.

[c] When the non-enveloped virus is a virus of the genus Vesivirus, at least one selected the group consisting of a persimmon extract, a catechin, an alkyl gallate (excluding that in the persimmon extract), pyrogallol, an organic acid and/or a salt thereof (excluding that in the persimmon extract) is used as the active ingredient.

[d] When the non-enveloped virus is a virus of the genus Rotavirus, at least one selected the group consisting of a persimmon extract, a catechin, pentagalloyl glucose, coffee tannin, an alkyl gallate (excluding that in the persimmon extract), pyrogallol, an organic acid and/or a salt thereof (excluding that in the persimmon extract) is used as the active ingredient.

[e] When the non-enveloped virus is a virus of the genus Betanodavirus, Aquavirnavirus, and/or Ranavirus, at least one selected the group consisting of a persimmon extract, wattle tannin, pentagalloyl glucose, and a catechin is used as the active ingredient.

[2] The antiviral agent according to [1], wherein the persimmon extract is prepared by heating a squeezed juice or an extract from a fruit of a plant of the genus *Diospyros* or treating the squeezed juice or the extract with an alcohol in order to inactivate an enzyme contained therein and derived from the plant of the genus *Diospyros*.

[3] The antiviral agent according to [1] or [2], wherein the persimmon extract contains at least condensed tannin.

[4] The antiviral agent according to any one of [1] to [3], wherein the persimmon extract is obtained from *Diospyros kaki*.

[5] The antiviral agent according to [1], wherein the catechin is at least one selected from the group consisting of catechin, epicatechin, epigallocatechin, epicatechin gallate, and epigallocatechin gallate.

[6] The antiviral agent according to [1], wherein the alkyl gallate is propyl gallate.

[7] The antiviral agent according to [1], wherein the organic acid and/or the salt thereof is an organic acid having 2 to 10 carbon atoms and/or a salt thereof.

[8] The antiviral agent according to [7], wherein the organic acid and/or the salt thereof is a hydroxyl-containing organic acid having 2 to 10 carbon atoms and/or a salt thereof.

[9] The antiviral agent according to [7] or [8], wherein the organic acid and/or the salt thereof is at least one organic acid selected from the group consisting of lactic acid, malic acid, citric acid, tartaric acid, salicylic acid, succinic acid, fumaric acid, and itaconic acid and/or a salt thereof.

[10] The antiviral agent according to any one of [1] to [9], wherein the antiviral agent includes an aqueous solution containing an organic acid and/or a salt thereof and having a pH of 4.5 or less.

[11] The antiviral agent according to any one of [1] to [10], wherein the non-enveloped virus is a non-enveloped virus belonging to the genus Betanodavirus, Aquavirnavirus, Ranavirus, Enterovirus, Mastadenovirus, Vesivirus, or Rotavirus.

[12] The antiviral agent according to [11], wherein the non-enveloped virus is nervous necrosis virus, infectious pancreatic necrosis virus, red seabream iridovirus, Coxsackie virus, adenovirus, feline calicivirus, or rotavirus.

[13] An antiviral alcohol preparation comprising at least the antiviral agent according to any one of [1] to [12] and an alcohol.

[14] The antiviral alcohol preparation according to [13], wherein the alcohol is ethanol and/or isopropanol.

[15] An antiviral washing composition comprising at least the antiviral agent according to any one of [1] to [12] and a surfactant.

[16] The antiviral washing composition according to [15], wherein the surfactant is an anionic surfactant and/or a nonionic surfactant.

[17] The antiviral washing composition according to [16], wherein the anionic surfactant and/or the nonionic surfactant is at least one surfactant selected from the group consisting of glycerin fatty acid partial esters, sorbitan fatty acid partial esters, and sucrose fatty acid partial esters.

[18] An antiviral disinfectant composition comprising at least the antiviral agent according to any one of [1] to [12] and an antimicrobial agent (excluding ethanol, an organic acid, and a salt thereof).

[19] The antiviral disinfectant composition according to [18], wherein the antimicrobial agent is at least one synthetic antimicrobial agent selected from the group consisting of isopropylmethylphenol, butyl p-hydroxybenzoate, and triclosan.

[20] A cosmetic composition comprising at least the antiviral agent according to any one of [1] to [12] and a humectant and/or a cosmetic fat and oil.

[21] The cosmetic composition according to [20], wherein the humectant is at least one humectant selected from the group consisting of propylene glycol, sorbitol, polyethylene glycol, hyaluronic acid, sodium chondroitin sulfate, ceramide, and aloe extract.

[22] The cosmetic composition according to [20], wherein beeswax is contained as the cosmetic fat and oil.

[23] An antiviral composition comprising at least the antiviral agent according to any one of [1] to [12], wherein the antiviral agent contains the persimmon extract at a ratio of 0.01 to 5% by weight (in terms of a solid content) based on the total composition.

[24] An antiviral composition comprising at least the antiviral agent according to any one of [1] to [12], the antiviral agent not containing an organic acid and/or a salt thereof, wherein the antiviral composition further contains an organic acid and/or a salt thereof.

[25] An antiviral composition comprising at least the antiviral agent according to any one of [1] to [12], wherein the antiviral composition contains an organic acid and/or a salt thereof and has a pH of 4.5 to 2.0.

[26] The antiviral composition according to any one of [23] to [25] further comprising vitamin C.

[27] A method for disinfection or infection control against a non-enveloped virus characterized by using an antiviral composition comprising the antiviral agent according to any one of [1] to [12].

[28] A therapeutic or prophylactic agent for an infectious disease caused by a non-enveloped virus, characterized by comprising the antiviral agent according to any one of [1] to [12] as an active ingredient.

The persimmon extract constituting the antiviral agent according to the present invention is preferably prepared by heating squeezed juice or an extract from a fruit of a plant of the genus *Diospyros* or treating the squeezed juice or the extract with an alcohol in order to inactivate an enzyme contained therein and derived from the plant of the genus *Diospyros*. The persimmon extract preferably contains at least condensed tannin and is, for example, an extract from *Diospyros kaki*.

In the antiviral agent according to the present invention, besides the persimmon extract, a catechin (catechin, epicatechin, epigallocatechin, epicatechin gallate, and epigallocatechin gallate, or the like), wattle tannin, pentagalloyl glucose, coffee tannin, an alkyl gallate (propyl gallate or the like), pyrogallol, an organic acid (citric acid or the like) and/or a salt thereof can be used as an active ingredient according to the intended non-enveloped virus.

Such an antiviral agent is preferably used as an active ingredient for the non-enveloped virus in a composition in combination with an alcohol, a surfactant, a bactericide, a humectant, a cosmetic fat and oil, or the like.

That is, an antiviral composition according to the present invention is characterized by containing at least the antiviral agent, and an alcohol, a surfactant, a bactericide, a humectant, or a cosmetic fat and oil. Such an antiviral composition preferably comprises the antiviral agent at a ratio of 0.01% to 5% by weight (in terms of solid content) based on the total composition. Preferably, the antiviral composition further comprises an organic acid and/or a salt thereof and further comprises vitamin C.

In one aspect of the present invention, the antiviral composition is provided as an antiviral alcohol preparation comprising at least the antiviral agent and an alcohol. The alcohol is preferably ethanol and/or isopropanol.

In one aspect of the present invention, the antiviral composition is provided as an antiviral washing composition (e.g., a hand soap) comprising at least the antiviral agent and a surfactant. The surfactant is preferably an anionic surfactant and/or a nonionic surfactant, and more preferably at least one surfactant selected from the group consisting of glycerin fatty acid partial esters, sorbitan fatty acid partial esters, and sucrose fatty acid partial esters.

In one aspect of the present invention, the antiviral composition is provided as an antiviral disinfectant composition comprising at least the antiviral agent and an antimicrobial agent. The antimicrobial agent is preferably at least one synthetic antimicrobial agent selected from the group consisting of isopropylmethylphenol, butyl p-hydroxybenzoate, and triclosan.

In one aspect of the present invention, the antiviral composition is provided as a cosmetic composition (a lotion, a milky lotion, a cream, or the like) comprising at least the antiviral agent, a humectant and/or a cosmetic fat and oil. The humectant is preferably aloe extract, and the cosmetic fat and oil is preferably beeswax.

The antiviral agent according to the present invention can also be used as an active ingredient of a therapeutic or prophylactic agent for infectious diseases caused by non-enveloped viruses. That is, a therapeutic or prophylactic agent for infectious diseases caused by non-enveloped viruses according to the present invention is characterized by comprising the antiviral agent as an active ingredient. In other words, in one aspect of the present invention, there is provided a method using the antiviral agent or the antiviral composition for disinfection and prevention of infection of the non-enveloped viruses.

Advantageous Effects of Invention

A persimmon extract, a catechin, wattle tannin, pentagalloyl glucose, coffee tannin, an alkyl gallate, pyrogallol, an organic acid and/or salt thereof used as an antiviral agent according to the present invention has much excellent effect on non-enveloped viruses than conventional bactericides, and is capable of killing 99% or more of non-enveloped viruses. Such an antiviral agent is not only directly used alone for disinfection or prevention of infection of the non-enveloped viruses but also very useful as an active ingredient of a composition, such as an alcohol preparation, a washing composition, a hand soap, a disinfectant composition, a lotion, a milky lotion, or a cream, or a pharmaceutical agent for the non-enveloped viruses.

In addition, since a persimmon extract (persimmon tannin), a catechin, an alkyl gallate (propyl gallate or the like), an organic acid and/or salt thereof (sodium citrate or the like) is approved as a food additive, all the components of the antiviral composition according to the present invention can be composed of food or food additives to produce a composition that causes no problem even if the composition adhering to food or dishes is ate or drunk. Use of the antiviral composition according to the present invention that contains such a persimmon extract, a catechin, an alkyl gallate, an organic acid and/or salt thereof as an active ingredient allows efficient disinfection and infection control against the non-enveloped viruses under circumstances where food is handled or in medical institutions, holding promise of greatly decreasing the incidence of diseases caused by the viruses.

DETAILED DESCRIPTION OF THE INVENTION

—Non-Enveloped Virus—

An antiviral agent and an antiviral composition according to the present invention can be applied over a wide range of non-enveloped viruses.

Known non-enveloped viruses include viruses of the families Iridoviridae, Adenoviridae, Polyomaviridae, and Papillomaviridae (having dsDNA); Circoviridae and Parvoviridae (having ssDNA); Reoviridae and Birnaviridae (having dsRNA); Picornaviridae, Caliciviridae, Hepaviridae, Astroviridae, and Nodaviridae (having positive sense strand ssRNA); and the like. The present invention can be intended for these non-enveloped viruses.

More specifically, examples of the non-enveloped viruses include non-enveloped viruses known as fish disease viruses belonging to the genera Betanodavirus (viral nervous necrosis virus (NNV) and the like), Aquavirnavirus (infectious pancreatic necrosis virus and the like), Aquareovirus, and Ranavirus (red seabream iridovirus (RSBI) and the like), the families Parvoviridae (Infectious hypodermal and hematopoietic necrosis virus (IHHNV) and the like) and Dicistroviridae (trout strawberry disease virus, Taura syndrome virus, and the like).

Other intended non-enveloped viruses include non-enveloped viruses known as human pathogenic viruses belong to the genera Enterovirus (Coxsackie virus, enterovirus, poliovirus, echovirus, and the like), Hepatovirus (hepatitis A virus and the like), Rhinovirus (rhinovirus and the like), Sapovirus (sapovirus and the like), Mamastrovirus (human astrovirus and the like), Papillomavirus (papillomavirus and the like), Polyomavirus (polyomavirus and the like), and Mastadenovirus (human adenovirus and the like), and Rotavirus (rotavirus and the like); feline calicivirus of the genus Vesivirus; and the like.

—Antiviral Agent—

Adaptability of Antiviral Agent to Intended Virus

With respect to adaptability of the antiviral agent according to the present invention to the intended non-enveloped viruses, at least one requirement selected from the group consisting of the following [a], [b], [c], [d], and [e] is satisfied.

[a] A persimmon extract is used as an active ingredient for a non-enveloped virus other than viruses of the genera Mastadenovirus, Vesivirus, Rotavirus, Betanodavirus, Aquavirnavirus, and Ranavirus.

[b] When the non-enveloped virus is a virus of the genus Mastadenovirus (human adenovirus or the like), at least one selected from the group consisting of a persimmon extract, a catechin, and wattle tannin is used as an active ingredient.

[c] When the non-enveloped virus is a virus of the genus Vesivirus (feline calicivirus or the like), at least one selected from the group consisting of a persimmon extract, a catechin, an alkyl gallate, pyrogallol, and an organic acid and/or a salt thereof is used as an active ingredient.

[d] When the non-enveloped virus is a virus of the genus Rotavirus, at least one selected from the group consisting of a persimmon extract, a catechin, pentagalloyl glucose, coffee tannin, alkyl gallates, pyrogallol, and an organic acid and/or a salt thereof is used as an active ingredient.

[e] When the non-enveloped virus is a virus of the genus Betanodavirus, Aquavirnavirus, and/or Ranavirus, at least one selected from the group consisting of a persimmon extract, wattle tannin, pentagalloyl glucose, and a catechin is used as an active ingredient.

Persimmon Extract

In the present invention, an extract from a plant of the genus *Diospyros* containing tannin, that is, a persimmon extract (also referred to as persimmon tannin), is used as the active ingredient of the antivirus agent. Not only a purified product of a substance derived from a plant of the genus *Diospyros* containing tannin, but also a mixture with a solvent used for extracting the substance, an alcohol used for alcohol treatment, or the like may be used as the persimmon extract.

Although the raw material for the persimmon extract is not particularly limited, use of an immature fruit of an astringent persimmon (e.g., *Diospyros kaki* Hachiya, Hiratanenashi, or the like) rich in persimmon tannin (particularly condensed tannin) is efficient and economical. A portion of a plant of the genus *Diospyros* other than fruit, such as leaves or bark, may be used as a raw material, provided that a persimmon extract composed of the same components can be produced.

Examples of a method for preparing a persimmon extract from such a raw material include, but not limited to, a method in which an astringent persimmon from which a calyx is removed is ground and squeezed to recover squeezed juice, a method in which an astringent persimmon from which a calyx is removed is cut into a suitable size, is processed into a liquid with a blender, and is centrifuged to recover the supernatant liquid, and a method for recovering an extract using water or an aqueous solvent from an astringent persimmon from which a calyx is removed.

Heating, Alcohol Treatment, and Other Treatments

Although a squeezed juice or an extract from the fruit of a plant of the genus *Diospyros* can be directly used as the persimmon extract according to the present invention, the squeezed juice or the extract is preferably treated by heating or with an alcohol in order to inactivate an enzyme contained therein and derived from the plant of the genus *Diospyros* (hereinafter also referred to as a "treated persimmon extract"). Heating or alcohol treatment can further improve the antiviral properties of the persimmon extract and prevent the verification measurement of antiviral properties from being interfered. Such a treated persimmon extract has the advantages of being relatively easily prepared and substantially free from color and odor issues when used as a component of the composition. The treated persimmon extract is therefore industrially easier to use than the astringent juice of the persimmon (described below) which takes time to ferment and is difficult to use in terms of color and odor.

The temperature and time conditions of the heat treatment may be such that an enzyme derived from a plant of the genus *Diospyros* contained in squeezed juice or the like can be inactivated and may be general conditions under which the enzyme can be inactivated. More specifically, the heat treatment may be generally performed at a temperature in the range of 60° C. to 130° C. for a time period in the range of 5 seconds to 30 minutes, for example, at 120° C. to 130° C. for 5 to 10 seconds or at approximately 85° C. for 5 to 15 minutes. Examples of the heat-treatment process include, but not limited to, heating in a process for sterilizing squeezed juice, heating in a powdering process, and heating before fermentation for producing the astringent juice of the persimmon (described in detail below).

On the other hand, the alcohol treatment may be generally performed with 30% to 100%, preferably 50% to 100%, alcohol, such as ethanol or the like. For example, persimmon squeezed juice is treated with substantially the same amount of 95 v/v % ethanol, and then the persimmon juice is preferably preserved in an airtight light-resistant container (usually resulting in a light-brown solution). The alcohol treatment process is also not limited to a particular process. For example, an extraction process using an alcohol solvent, such as ethanol or the like, corresponds to the alcohol treatment process. Typically, as a process for producing an alcohol preparation as an antiviral composition according to the present invention, an alcohol treatment process can be performed by adding an alcohol to a persimmon extract, which is, if necessary, heat-treated as described above. Such an alcohol treatment also has a sterilization effect on saprophytic bacteria in a persimmon extract.

Alternatively or in addition, the persimmon extract according to the present invention may be subjected to concentration, solidification by drying or lyophilization, and powdering by grinding (the color of a lyophilized powder is generally light yellow), or purification using an ion-exchange resin, if necessary, without compromising the advantages of the present invention. Since the persimmon extract contains much polyphenol, a liquid persimmon extract is which catechin, catechin gallate, gallocatechin, and gallocatechin gallate are condensed via carbon-carbon bonds at a ratio of approximately 1:1:2:2 (Matsuo & Itoo (1981): see Non-patent Literature 1 cited above).

[Formula 1]

Probable Structural Formula of Persimmon Condensed Tannin liable to undergo deterioration, such as coloring or the like. The persimmon extract is therefore preferably preserved in a solid state in frozen storage by lyophilization. Preferably, these procedures are performed under mild conditions such that tannin and other components in the persimmon extract are not decomposed.

The persimmon extract in the present invention may be "the astringent juice of the persimmon" which is a liquid produced by fermenting and aging squeezed juice of an immature astringent persimmon for a long period of time (approximately 1 to 3 years) and which contains several percent solid (persimmon tannin) and an organic acid produced by the fermentation. The astringent juice of the persimmon has been used as folk medicine or a paint and is commercially available as a commodity, such as "Kakishibu" (Toyama Kakishibu Seizojo). Alternatively, a fermented product prepared by adding a yeast culture solution derived from a persimmon to persimmon juice and fermenting it at a temperature in the range of 20° C. to 25° C. for 1 to 3 months may be used (a reddish-brown liquid is usually produced). Then, the fermented product is preferably preserved in an airtight container.

An additive described as "persimmon tannin" (Name/Synonym=The astringent juice of the persimmon, a persimmon extract. Origin/Preparation/Nature=Squeezed juice of the fruit of *Diospyros kaki* THUNB., or a water or ethanol extract. The main component is tannin or tannic acid.) in "List of Existing Food Additives" based on the Food Sanitation Act in Japan may also be used as the persimmon extract in the present invention.

Persimmon Tannin

A plant of the genus *Diospyros*, particularly its fruit, is rich in substances having certain properties, such as astringency and affinity for metal ions, and responsible for astringency, that is, compounds collectively referred to as tannin. In many instances, persimmon tannin characteristically contains, as a major component, "persimmon condensed tannin" having the following probable structural formula (1), which is composed of catechin, gallocatechin, and gallic acid esters thereof. For example, persimmon condensed tannin contained in the fruit of *Diospyros kaki*, which is a plant of the genus *Diospyros* native to China and is cultivated worldwide, including Japan, is a high-molecular compound in In addition to the "persimmon condensed tannin" described above, persimmon tannin sometimes contains another tannin compound, such as catechin or hydrolyzable tannin.

Hydrolyzable tannin is an ester between an alcohol (such as glucose) and a carboxylic acid (such as gallic acid) or an oligomer thereof and is depolymerized by hydrolysis. In contrast, persimmon condensed tannin is not depolymerized by hydrolysis (the basis carbon-carbon skeleton of the polymer is not hydrolyzed). The persimmon condensed tannin can therefore be differentiated from the hydrolyzable tannin and can be purified and quantified by, for example, a method described in Matsuo & Itoo (1981b) (Non-patent Literature 2 cited above).

To develop antiviral properties for non-enveloped viruses in the present invention, although it is assumed that a persimmon extract preferably contains at least the persimmon condensed tannin, possible contribution of another component in the persimmon extract is not excluded. In general, the persimmon extract prepared by a method described below using the fruit of *Diospyros kaki* spontaneously contains persimmon condensed tannin. Thus, it is assumed that the antiviral agent according to the present invention is preferably produced using such a persimmon extract as a raw material.

Catechin

When the antiviral agent according to the present invention is intended for a non-enveloped virus of the genus Betanodavirus, Aquavirnavirus, Ranavirus, Mastadenovirus, Vesivirus, or Rotavirus, catechin contained in a plant, such as catechu (also referred to as "gambir", botanical name "*Acacia Catechu*") which is a shrub of the leguminous genus *Acacia* indigenous to India, a tea tree (botanical name "*Camellia Sinensis*"), or the like, may be used as the active ingredient.

"Catechins" is a generic name of 3,5,7,3',4'-pentahydroxyflavan (catechin in a narrow sense), 3,5,7,3',4',5'-hexahydroxyflavan (gallocatechin), and 3-galloyl derivatives thereof, and includes stereoisomers thereof.

For example, (+)-catechin isolated from catechu has the following structural formula (2).

[Formula 2]

Structural Formula (2)

Catechins (also referred to as "green tea tannin") contained in a tea tree contain as major components epicatechin (structural formula (3)) and its hydroxy derivative, epigallocatechin (structural formula (4)), and gallates thereof, i.e., epicatechin gallate (structural formula (5)) and epigallocatechin gallate (structural formula (6)). These compounds may be isomerized by heat treatment.

[Formula 3]

Structural Formula (3)

[Formula 4]

Structural Formula (4)

[Formula 5]

Structural Formula (5)

[Formula 6]

Structural Formula (6)

Catechins are also contained in other plants. In the present invention, these compounds isolated from a plant containing catechins may be used or an extract from a plant containing catechins may be used. Any one of catechins may be used or a combination of two or more may be used. Catechins contained in a tea tree are most preferably used.

Wattle Tannin

When the antiviral agent according to the present invention is intended for a non-enveloped virus of the genus Betanodavirus, Aquavirnavirus, Ranavirus, Mastadenovirus, or Rotavirus, wattle tannin can be further used as the active ingredient.

Wattle tannin is tannin extracted from bark, leaves, seedpods of a plant of the genus *Acacia*, for example, derived from *Acacia pycnantha* (Golden Wattle), *Acacia decurrens* (Tan Wattle), *Acacia dealbata* (Silver Wattle, also referred to as "Mimosa Wattle"), *Acacia mearnsii* (Black Wattle), or the like.

Pentagalloyl Glucose

When the antiviral agent according to the present invention is intended for a non-enveloped virus of the genus Betanodavirus, Aquavirnavirus, Ranavirus, or Rotavirus, pentagalloyl glucose can be further used as the active ingredient.

Pentagalloyl glucose is a compound in which gallic acid is ester-bonded to hydroxyl groups (1-, 2-, 3-, 4-, and 6-positions) of glucose and is produced by, for example, decomposing and purifying gallnut tannin used as a raw material.

Coffee Tannin

When the antiviral agent according to the present invention is intended for a non-enveloped virus of the genus Rotavirus, coffee tannin can be further used as the active ingredient.

Coffee tannin is tannin (or a tannin-like substance) extracted from coffee beans or the like and mainly contains chlorogenic acid (compound in which coffeic acid is ester-bonded to a hydroxyl group (any one or more of the 3-, 4-, and 5-positions) of quinic acid).

Alkyl Gallate

When the antiviral agent according to the present invention is intended for a non-enveloped virus of the genus Vesivirus or Rotavirus, an alkyl gallate (an ester compound of gallic acid (3,4,5-trihydroxybenzenecarboxylic acid) and an alcohol, excluding the above-described pentagalloyl glucose and epicatechin gallate and epigallocatechin gallate included in the catechins) can be further used as the active ingredient (excluding a case in which a persimmon extract originally containing an alkyl gallate is used).

Examples of the alkyl gallate include ethyl gallate, n-propyl gallate, n-butyl gallate, n-pentyl gallate, n-octyl gallate, n-nonyl gallate, n-decyl gallate, isobutyl gallate, isoamyl gallate, and the like. For example, n-butyl gallate is preferred. In addition, alkyl gallates (n-propyl gallate and the like) are also used as an antioxidant (food additive).

Pyrogallol

When the antiviral agent according to the present invention is intended for a non-enveloped virus of the genus Vesivirus or Rotavirus, pyrogallol (1,2,3-trihydroxybenzene) can be further used as an active ingredient.

Organic Acid and/or Salt Thereof

When the antiviral agent according to the present invention is intended for a non-enveloped virus of the genus Vesivirus or Rotavirus, an organic acid and/or a salt thereof can be further used as an active ingredient (excluding a case in which the persimmon extract (particularly the astringent juice of the persimmon) originally containing an organic acid and/or a salt thereof is used).

The organic acid and/or salt thereof is preferably an organic acid having 2 to 10 carbon atoms and/or a salt thereof, and more preferably a hydroxyl-containing organic acid having 2 to 10 carbon atoms and/or a salt thereof. More specifically, at least one organic acid selected from the group consisting of lactic acid, malic acid, citric acid, tartaric acid, salicylic acid, succinic acid, fumaric acid, and itaconic acid and/or a salt thereof is preferred, and particularly citric acid or a salt thereof is preferred. A salt of an organic acid is preferably a sodium salt, a potassium salt, or the like of the organic acid.

When the antiviral agent according to the present invention is intended for a non-enveloped virus of the genus Vesivirus or Rotavirus, a solution containing an organic acid and/or a salt thereof used as an active ingredient preferably has a pH of 4.0 or less and more preferably 2.0 to 4.0. The pH of an aqueous solution of the antiviral agent can be measured with a general pH meter (e.g., a pH meter manufactured by Beckmann Coulter Inc.). When the antiviral agent is used singly, the pH of the antiviral agent is preferably adjusted within the above-described range. However, when the antiviral agent is mixed (diluted) in an antiviral composition, the pH of the antiviral agent may be previously adjusted within a range lower than the above-described range according to demand so that the final pH of the composition is in the preferred range.

—Antiviral Composition—

The antiviral composition according to the present invention comprises the antiviral agent as an active ingredient for the non-enveloped virus, and at least one component selected from alcohols, surfactants, bactericides, humectants, and cosmetic fats and oils and, if necessary, further comprises citric acid and/or a salt thereof or vitamin C. Although the antiviral composition according to the present invention is not limited to a particular aspect, representative aspects are as follows:

An alcohol preparation that comprises at least the antiviral agent and an alcohol.

A washing composition that comprises at least the antiviral agent and a surfactant.

A disinfectant composition that comprises at least the antiviral agent and an antimicrobial agent.

A cosmetic composition (a lotion, a milky lotion, a cream, or the like) that comprises at least the antiviral agent and a humectant and/or a cosmetic fat and oil.

The washing composition according to one aspect of the present invention can remove contamination of food, dishes, cooking utensils, breeding instruments and breeding water tanks for fishes, fingers of workers, and clothes and kill non-enveloped viruses. For example, the washing composition is provided as a liquid or solid detergent. The alcohol preparation and the disinfectant composition according to other aspects of the present invention are used to inactivate the non-enveloped viruses and bacteria deposited on food, dishes, cooking utensils, breeding instruments and breeding water tanks for fishes, fingers of workers, and instruments with which the excreta of patients are treated. For example, like conventional ethanol preparations, the alcohol preparation and the disinfectant composition are provided as sprays. The washing composition or the disinfectant composition according to another aspect of the present invention can be used for killing viruses which infect eggs of fishes, young and larval fishes, or parent fishes. The cosmetic composition (a lotion, a milky lotion, a cream, or the like) according to a still another aspect of the present invention can be applied to fingers of workers that tend to be chapped from washing to improve the condition of the skin and can kill the non-enveloped viruses (basic skin-care preparation).

It goes without saying that an alcohol, a surfactant, a bactericide, a humectant, and a cosmetic fat and oil may be used in combination in the antiviral composition according to the present invention. For example, the alcohol preparation preferably further comprises a surfactant, such as a fatty acid ester or the like, to improve antimicrobial properties. According to other aspects of the present invention, the washing composition can be a hand soap that comprises a bactericide or an alcohol, as well as a surfactant, and the cream can contain an antimicrobial agent or an alcohol for keeping the skin clean, as well as a component for protecting the skin.

In addition to the components specifically described herein, the antiviral composition according to the present invention may appropriately comprise a component for imparting a desired capability to improve the quality of the composition, for example, a thickener (such as xanthan gum, locust bean gum, sodium polyacrylate, or the like), an antioxidant, a perfume, and/or a dye, and cosmetics, such as a lotion and the like, may appropriately comprise a barrier cream and/or an antiphlogistic agent.

Amount of Antiviral Agent

The amount of the antiviral agent in the antiviral composition according to the present invention can be appropriately adjusted in a manner that depends on the component ratios of the composition and a method for using the composition, provided that the composition has antiviral properties for non-enveloped viruses, and may be such that the amount of the active ingredient, such as the persimmon extract, catechin, or the like, in the antiviral agent preferably ranges from 0.01% to 5% by weight, more preferably 0.1% to 2% by weight, still more preferably 0.2% to 2% by weight, most preferably 0.5% to 2% by weight, of the total amount of the antiviral composition.

The amount of the antiviral agent is based on a "solid". For example, when a liquid substance, such as a persimmon fruit extract, an extract from a plant containing catechins such as a tea tree, or the like, is used as a raw material, the amount of the liquid substance is controlled such that the weight of a solid (a powder produced by drying or lyophilization) in the liquid substance is in the range described above. In general, squeezed juice of a persimmon fruit contains approximately 5% to 10% solid.

Organic Acid and/or Salt Thereof

When a persimmon extract (persimmon tannin), catechin, wattle tannin, pentagalloyl glucose, coffee tannin, an alkyl gallate, or pyrogallol is used as the active ingredient of the antiviral agent, but an organic acid and/or a salt thereof is not used, the antiviral composition according to the present invention preferably comprises an organic acid and/or a salt thereof in addition to the antiviral agent. An organic acid and/or a salt thereof independently has no antiviral properties depending on the type of the non-enveloped virus. However, in combination with the persimmon extract, the organic acid and/or a salt thereof may further increase the efficacy of the persimmon extract and the like. In this case, usable organic acids and/or salts thereof are the same as those described above as an active ingredient for the specified non-enveloped viruses. In particular, citric acid and/or a salt thereof is preferred.

Organic acids and/or salts thereof are substances excellent in antimicrobial activity against bacteria, are approved as food additives, and function to enhance the solubility of tannin and function as chelating agents for preventing coloring of tannin in contact with iron.

The amount of the organic acid and/or a salt thereof added preferably ranges from 0.05% to 5.0% by weight, more preferably 0.1% to 2.0% by weight, of the total amount of the antiviral composition (including a solvent). When the organic acid and/or a salt thereof is used for the above-described purpose in an aqueous solution composition, not as an active ingredient for non-enveloped viruses of the genus Vesivirus or Rotavirus, the amount of organic acid and/or a salt thereof is preferably such that the pH ranges from 2.0 to 6.0, preferably 2.0 to 4.5, more preferably 2.0 to 4.0.

Vitamin C

In addition to the antiviral agent described above, the antiviral composition according to the present invention preferably comprises vitamin C, which is known as an antioxidant to be added to food. "Vitamin C" is a generic name and includes DL-ascorbic acid and ascorbic acid esters (such as palmitate), as well as L-ascorbic acid which is generally referred to as vitamin C. Vitamin C can prevent oxidation of the persimmon extract (particularly persimmon tannin), ensure stable and persistent efficacy against non-enveloped viruses, and prevent reddening due to oxidation.

The amount of vitamin C added preferably ranges from 0.01% to 3.0% by weight, more preferably 0.05% to 1.0% by weight, of the total amount of the antiviral composition (including a solvent).

Alcohol

The alcohol may be an alcohol used in general alcohol preparations and is preferably ethanol and/or propanol, which has an excellent antimicrobial activity against bacteria and is approved as a food additive. The concentration of the alcohol may be substantially the same as in general alcohol preparations, can be adjusted in consideration of antimicrobial activity, and preferably ranges from approximately 20% to 80% of the total amount of alcohol preparation. An alcohol may be used as a solvent in a composition other than alcohol preparations and may be contained in cosmetics as a component for imparting astringency to the skin or an antiseptic property.

Surfactant

Surfactants include cationic, anionic, amphoteric, and nonionic surfactants. Taking the chemical properties of persimmon condensed tannin (polyphenol), catechin, tannic acid, gallates, pyrogallol, or an organic acid and/or a salt thereof into account, an anionic surfactant and/or a nonionic surfactant is preferably used in the present invention.

Examples of the anionic surfactant include soap (alkali salts of higher fatty acids), monoalkyl sulfates, alkyl polyoxyethylene sulfates, alkylbenzene sulfonates, and monoalkyl phosphates.

Examples of the nonionic surfactant include polyoxyethylene alkyl ethers, polyoxyethylene fatty acid esters, fatty acid partial esters of polyhydric alcohols (such as glycerin and sugar alcohol), and fatty acid diethanolamides.

Among these surfactants, surfactants approved as food additives, such as glycerin fatty acid partial esters, sorbitan fatty acid partial esters, and sucrose fatty acid partial esters, are preferred in the present invention because these surfactants present no problem even if they are deposited on food, dishes, or cooking utensils.

The surfactants also destroy cell membranes of bacteria or envelopes of viruses (other than the intended non-enveloped viruses of the present invention). For example, partial esters of glycerin and fatty acids having 6 to 18 carbon atoms have high antimicrobial activity against *Escherichia coli* and *Staphylococcus aureus*. Thus, the alcohol preparation preferably comprises such a surfactant. The surfactants are also used to mix an oil phase and an aqueous phase in creams and milky lotions.

Antimicrobial Agent

Antimicrobial agents (including substances called bactericides and disinfectants) other than ethanol and citric acid described above for use in the present invention are not particularly limited. Examples of preferred antimicrobial agents include antimicrobial agents that are efficacious against *Escherichia coli, Staphylococcus aureus*, MRSA, *Salmonella, Vibrio parahaemolyticus*, or *Pseudomonas aeruginosa*, which causes problems of infection in food processing or nosocomial infection. Examples of such antimicrobial agents are as follows:

Natural antimicrobial agents: proteins (such as milt protein and egg-white lysozyme) and peptides (such as polylysine);

Antibiotics: penicillin antibiotics, chloramphenicol, streptomycin, tetracycline antibiotics, and cephalosporin antibiotics; and Synthetic antimicrobial agents: chlorine compounds (such as triclosan), iodine compounds (such as povidone-iodine), zinc compounds (such as zinc cetylpyridinium), benzenecarboxylic acids (such as benzoic acid, salicylic acid, isopropylmethylphenol, and butyl p-hydroxybenzoate (=butylparaben)), organic acid esters (such as glycerin esters and sucrose esters), aldehydes (such as glutaraldehyde and formaldehyde), biguanide compounds (such as chlorhexidine gluconate), and quaternary ammonium salts (such as benzalkonium chloride and cetylammonium bromide).

Among these antimicrobial agents, isopropylmethylphenol, butyl p-hydroxybenzoate, and triclosan are preferred in the present invention because of strong antimicrobial action and high compatibility with a persimmon extract.

A substance that can be used as an antimicrobial agent as described above may be contained in the ethanol preparation described above and is sometimes used as an antiseptic in cosmetics.

Humectant

Humectants (wetting agents) that can be used in the present invention are those used in cosmetics such as, general lotions, milky lotions, and creams, and include glycerin, propylene glycol, sorbitol, polyethylene glycol, hyaluronic acid, sodium chondroitin sulfate, ceramide, and an aloe extract. Among these humectants, humectants approved as food or food additives, such as an aloe extract, are preferred in the present invention because they cause no problem even if they adheres to food, dishes, or cooking utensils.

Cosmetic Fats and Oils

Cosmetic fats and oils form a film on the skin to protect the skin and impart flexibility, smoothness, and gloss to the skin. Cosmetic fats and oils also impart moderate availability to cosmetics. In the present invention, cosmetic fats and oils used in cosmetics, such as general milky lotions and creams, can be used. Examples of the cosmetic fats and oils are as follows:

Fats and oils (esters of higher fatty acids and glycerin): vegetable oils and fats, animal oils and fats, hydrogenated compounds thereof (such as partially hydrogenated rapeseed oil), and synthetic triglyceride (such as tri(capryl/capric acid)glyceryl);

Wax (esters of higher fatty acids and higher alcohols, the esters being solid at normal temperature): vegetable wax and animal wax (such as beeswax and lanolin);

Hydrocarbons: mineral hydrocarbons (such as liquid paraffin, vaseline, and paraffin) and animal hydrocarbons (such as squalane);

Higher fatty acids: lauric acid, myristic acid, palmitin acid, stearic acid, oleic acid, and isostearic acid;

Higher alcohols: cetanol, stearyl alcohol, and lanolin alcohol; and

Esters (esters of fatty acids and alcohols other than wax): myristyl myristate, propylene glycol dioleate, and cetyl lactate.

Among these, cosmetic fats and oils approved as food or food additives, such as beeswax, are preferred in the present invention because these cosmetic fats and oils cause no problem even if they adheres to food, dishes, or cooking utensils.

Manufacturing Method

A method for manufacturing the antiviral composition according to the present invention is the same as a method for manufacturing a conventional alcohol preparation, detergent, disinfectant, or a cosmetic (lotion, milky lotion, or cream), except that the antiviral agent (persimmon extract) is comprised as a raw material and, if necessary, citric acid and/or a salt thereof or vitamin C is comprised, and accordingly additional adjustments are appropriately made. The antiviral composition according to the present invention can be produced using the antiviral agent, in addition to general (or, if necessary, finely adjusted) raw materials of these conventional products by the same (or, if necessary, finely adjusted) manufacturing process as that for conventional products. For example, a cream according to one aspect of the present invention may be produced by adding the antiviral agent and other components to purified water to prepare an aqueous phase, preparing an oil phase composed of a cosmetic fat and oil and other materials, and mixing the aqueous phase and the oil phase at a predetermined ratio.

A method for using the antiviral composition according to the present invention is also the same as a method for using a conventional alcohol preparation, detergent, disinfectant, or a cosmetic (lotion, milky lotion, or cream). The antiviral composition according to the present invention can be commercialized in accordance with a suitable aspect depending on a method for using the antiviral composition. For example, a detergent may be a concentrated detergent, which is diluted before use; and an alcohol preparation or a disinfectant may be of a spray type or a wiper in which a nonwoven fabric is impregnated with the alcohol preparation or the disinfectant.

When the antiviral agent or the antiviral composition according to the present invention comprises an organic acid and/or a salt thereof, the organic acid and/or a salt thereof is preferably added in such an amount that the pH of an aqueous solution ranges from 2.0 to 4.5, more preferably 2.0 to 4.0 (particularly for non-enveloped viruses belonging to the genus Vesivirus or Rotavirus).

Pharmaceutical Agent

The antiviral agent according to the present invention can be used as an active ingredient of a therapeutic or prophylactic agent for an infectious disease caused by the non-enveloped viruses. The dosage form of such a pharmaceutical agent can be appropriately selected from, for example, oral ingestion forms, such as a liquid, a syrup, a tablet, a capsule, a powder, and granules, and an injection, and can be produced by a general preparation method, if necessary, in combination with various additive agents, such as an excipient (for example, lactose or another saccharide), a binder (for example, starch, methylcellulose, or poly(vinyl alcohol)), a stabilizer (for example, ascorbic acid), a preservative (for example, p-hydroxybenzoate), a sweetener, and/or a solvent. The effective dose of such a pharmaceutical agent can be appropriately determined in accordance with the age, the body weight, and the symptom of a patient, the administration route, the administration schedule, and the formulation of the pharmaceutical agent, and the inhibitory activity of materials. The amount of antiviral agent in a pharmaceutical agent may be adjusted to these conditions.

The antiviral agent according to the present invention and a pharmaceutical agent comprising the antiviral agent can take not only an administration form for humans but also an administration form for animals other than humans, such as mammals and fishes which are possibly infected with non-enveloped viruses. Examples of a method which can be applied to fishes include a method of orally administrating a mixture containing a bait and the antiviral agent or a pharmaceutical agent comprising the antiviral agent, a method of forcibly orally administering the antiviral agent or a pharmaceutical agent comprising the antiviral agent using a syringe, or a method using a "medicated bath" in which fishes are bred for a certain time or constantly in breeding water containing the antiviral agent.

EXAMPLES

Preparation of Persimmon Extract (a) Persimmon juice fermented liquid (for HA-23): a ground product of an immature fruit of *Diospyros kaki* (astringent persimmon) was charged in a fine-weave cloth bag and was squeezed. The resultant squeezed juice was charged in a glass vessel and was naturally fermented for approximately one year. A solid was then filtered off to prepare a reddish-brown solution. The solution contained approximately 10% solid component (a persimmon extract), and approximately half (approximately 5%) of the solid component was persimmon tannin.

(b) Persimmon juice FD powder (for HA-72A/HA-201): an immature fruit of persimmon from which a calyx was removed and which was sufficiently sterilized sodium hypochlorite (NaClO), washed, and treated (vitamin C) for preventing coloring was diced and crushed. The resultant fruit/fruit juice solution was passed through a 200-mesh sieve, centrifuged, sterilized at a high temperature (120° C. to 130° C., 7 to 10 seconds), and then freeze-dried to prepare a powdery persimmon extract.

Preparation of Reagent

Reagents according to the component ratios shown in Table 1 were prepared and used for verification of the effect on fish disease viruses or human pathogenic viruses described below (Examples 1 to 5).

TABLE 1

Component Ratios of Reagent (the remainder is water)

| | Persimmon extract/ Control | | Ethanol | Citric acid | Trisodium citrate | Glycerin mono-caprate*[6] |
|---|---|---|---|---|---|---|
| HA-23 | Persimmon juice fermented liquid (solid content 1%) | 10% | 50% | 1.6% | 0.5% | 0.5% |
| HA-72A | Persimmon juice FD powder | 0.3% | 50% | 1.6% | 0.5% | 0.5% |
| HA-201 | Persimmon juice FD powder | 1% | 50% | — | — | — |
| HA-2*[1] | Gallnut tannin*[2] | 0.5% | 51% | 1.6% | 0.5% | 0.6% |
| HA-16 | Pentagalloyl glucose | 1% | 50% | 1.6% | 0.5% | 0.5% |
| HA-17 | Wattle tannin*[3] | 1% | 50% | 1.6% | 0.5% | 0.5% |
| HA-18 | Coffee tannin*[4] | 1% | 50% | 1.6% | 0.5% | 0.5% |
| HA-19 | Propyl gallate | 1% | 50% | 1.6% | 0.5% | 0.5% |
| HA-20 | Green tea tannin*[5] | 1% | 50% | 1.6% | 0.5% | 0.5% |
| HA-21 | Pyrogallol | 1% | 50% | 1.6% | 0.5% | 0.5% |
| HA-22 | Gallic acid | 1% | 50% | 1.6% | 0.5% | 0.5% |
| HA-202 | — | — | 50% | 1.6% | 0.5% | 0.3% |

*[1]HA-2: further comprising 0.15% glycerol (glycerin).
*[2]Gallnut tannin: trade name "Tannic acid AL" (Fuji Chemical Industry Co., Ltd.), tannin derived from gallnut (insect gall of sumac).
*[3]Wattle tannin: trade name "Tannic acid ME-S" (Fuji Chemical Industry Co., Ltd.), tannin derived from mimosa *acacia*.
*[4]Coffee tannin: trade name "Cafenol" (Fuji Chemical Industry Co., Ltd.), tannin derived from green coffee beans.
*[5]Green tea tannin: trade name "Catechin FP95" (Fuji Chemical Industry Co., Ltd.), tannin derived from green tea.
*[6]Glycerin monocaprate: trade name "Poem M-200" (Riken Vitamin Ltd.).

TABLE 2

Characteristics of Viruses and Fish Cultured Cells Used

| Virus | Particle shape | Envelope | Nucleic acid (polarity) | Cultured cell (biological origin) |
|---|---|---|---|---|
| NNV | Spherical | No | ssRNA (+) | E-11 (*Ophicephalus striatus*) |
| ABV | Spherical | No | dsRNA (+/−) | RTG-2 (*Oncorhynchus mykiss*) |
| RSIV | Spherical | No | dsDNA (+/−) | GF (*Haemulon sciurus*) |

Example 1

Verification of Effect on Fish Disease Virus (1) Viruses Used

The characteristics of the viruses used are shown in Table 2. Viral nervous necrosis caused by viral nervous necrosis virus (NNV) (Schneemann et al., 2005) is a disease which occurs in various marine fishes at a very high death rate. Aquavirnavirus (ABV) (Nguyen et al., 1994) is a spherical virus which has a genome composed of double-stranded DNA and which causes infectious pancreatic necrosis in fishes, such as brook trout, rainbow trout, eel, flounder, and the like. Red seabream iridovirus (RSIV) (Kazuhiro NAKAJIMA, Jun KURITA, 2005) causes red seabream iridovirus disease, but this disease occurs in not only red seabream but also various fishes such as yellowtail, amberjack, sea bass, and the like. This disease is one of the diseases with the largest number of reported victims among the fish diseases in Japan.

(2) Mixing of Virus and Test Reagent

Among the above-described reagents prepared according to the compositions, each of the reagents shown in Table 3 was diluted with Hanks' balanced salt solution (Nissui) (HESS) and adjusted so that the concentration of a persimmon extract or a control was 0.3% or 0.03%. Fifty microliters of each virus solution was mixed with 50 μL each of the reagents (the final concentration of the persimmon extract or the control was 0.15% or 0.015%), and the resultant mixture was allowed to stand at room temperature for 2 minutes. Then, 9.9 mL of HBSS was added to the mixture to terminate reaction, and a 10-fold dilution series of the sample was prepared using HBSS.

(3) Test of Measuring Viral Titer Using Fish Cultured Cells

The fish cultured cells shown in Table 2 were inoculated in a 96-well plate (IWAKI) to be 80% confluent, and 90 μL of a medium was added to each well, followed by culture for 24 hours. The medium used was L-15 (for E-11), MEM (for RTG-2), or BME (for GF). Then, 10 μL of the dilution series solution previously prepared was inoculated in each well, and culture was further performed for 10 days to confirm the appearance of a cytopathic effect (index for viral infection).

Then, a limit dilution point where the cytopathic effect was not observed was confirmed, and a viral titer was measured according to a Reed and Muench method (1938). A ratio of the viral titer in a test area to the viral titer in a control area (100%) was calculated to evaluate the antiviral effect.

(4) Experiment Result

The antiviral action of each of the reagents was as shown in Table 3.

TABLE 3

| | Antiviral Effect of Test Reagent* | | | | |
|---|---|---|---|---|---|
| | | NNV | ABV | RSIV | |
| | Test reagent | 0.15% | 0.15% | 0.15% | 0.015% |
| HA-72A | (persimmon juice FD powder) | 1.0 | 0.5 | 0.32 | 0.32 |
| HA-23 | (persimmon juice fermented liquid) | 10.0 | 0.5 | 10 | 32 |
| HA-16 | (pentagalloyl glucose) | 3.9 | 17.0 | 10 | 32 |
| HA-17 | (wattle tannin) | 1.0 | 3.0 | 0.21 | 0.32 |
| HA-18 | (coffee tannin) | 143.1 | 17.0 | 100 | 100 |
| HA-19 | (propyl gallate) | 39.2 | 36.3 | 32 | 100 |
| HA-20 | (green tea tannin) | 10.9 | 5.4 | 6.6 | 10 |
| HA-21 | (pyrogallol) | 83.8 | 17.0 | 32 | 100 |
| HA-22 | (gallic acid) | 143.1 | 79.4 | 65.8 | 100 |
| HA-2 | (gallnut tannin) | 65.8 | 10.7 | 100 | 100 |

*Residual viral titer based on 100% of a control without treatment of virus. For RSIV, an area of 0.015% treatment concentration was provided.

Example 2

Verification of Effect on Human Pathogenic Virus (Coxsackie Virus)

(1) Test Virus

Coxsackie virus group B, type 5
(non-enveloped virus, clinical isolate, 2 passages in FL cells derived from aseptic meningitis of a 2-year-old girl)

(2) Method for Measuring Viral Infectivity

The FL cells were infected with the virus, and a 50% infection dose (unit: 50% tissue culture infectious dose [TCID50]) was calculated.

FL cells: Cell line contaminated with HeLa cells (derived from human cervical cancer epithelial cells).

(3) Test Method

To eliminate the influence of serum contained in original viruses, a virus solution was previously 50 times diluted with PBS. Then, equal amounts (100 μL) of the diluted virus solution, each of the reagents shown in Table 4 among the reagents prepared according to the above component ratios, PBS, and 50% (v/v) ethanol were mixed, followed by reaction at room temperature for 3 minutes. A 10-fold dilution series was formed using a diluent and inoculated in cells in a 96-well plate. Several days after, extension of CPE was observed to measure viral infectivity.

Diluent: Dulbecco's modified Eagle's minimum essential medium, penicillin G, streptomycin, amphotericin B (serum-free)

Figure 1:
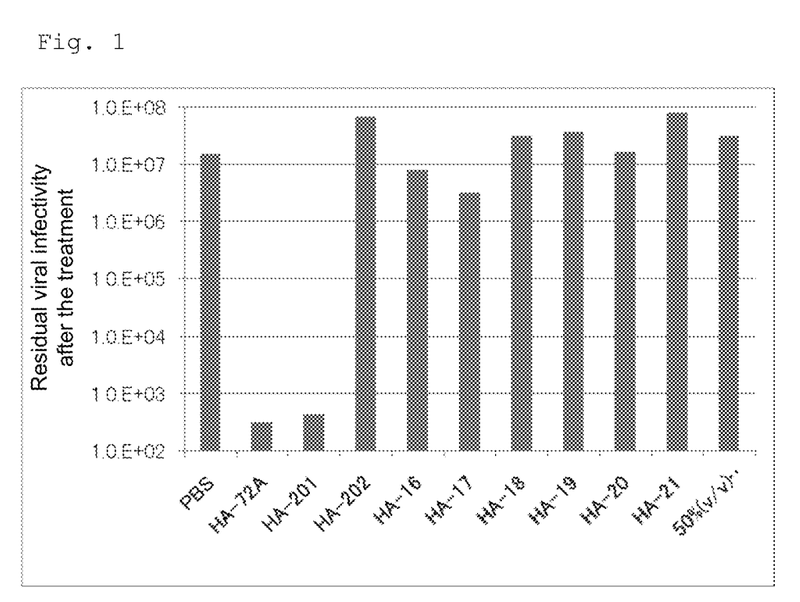
FIG. 1 is a graph showing the results of measurement of viral infectivity of Coxsackie virus in Example 2.

The results were as shown in Table 4 and FIG. 1.

The Coxsackie virus infectivity was suppressed to 1/30,000 to 1/50,000 or more with HA-72A and HA-201 (persimmon extract), and thus strong antiviral activity was observed. On the other hands, such antiviral activity was not observed with the other reagents. It is thus considered that the persimmon extract mainly contributes to antiviral activity, while citric acid and ethanol have no anti-Coxsackie virus activity. Although viral infectivity appears to remain after treatment even with HA-72A and HA-201, this is the level of cytotoxicity due to the reagents but is not necessarily due to viruses. It is consistent to think that the viruses are substantially completely inactivated.

TABLE 4

| Reagent | | Infectivity | Infectivity | Effect (times) |
|---|---|---|---|---|
| Name | Concentration | (TCID50/ml) | ratio (to PBS) | (to PBS) |
| PBS | 1x | 1.8E+07 | 1.00000 | 1 |
| HA-72A | Stock solution | 3.2E+02 | 0.00002 | 56234 |
| HA-201 | Stock solution | 5.6E+02 | 0.00003 | 31623 |
| HA-202 | Stock solution | 3.2E+07 | 1.77828 | 1 |
| HA-16 | Stock solution | 1.0E+07 | 0.56234 | 2 |
| HA-17 | Stock solution | 3.2E+06 | 0.17783 | 6 |
| HA-18 | Stock solution | 3.2E+07 | 1.77828 | 1 |
| HA-19 | Stock solution | 1.8E+07 | 1.00000 | 1 |
| HA-20 | Stock solution | 1.8E+06 | 0.10000 | 10 |
| HA-21 | Stock solution | 5.6E+07 | 3.16228 | 0 |
| Ethanol | 50% (v/v) | 3.2E+07 | 1.77828 | 1 |

Example 3

Verification of Effect on Human Pathogenic Virus (Adenovirus)

(1) Test Virus

Adenovirus (non-enveloped virus, nonproliferating adenovirus that expresses adenovirus type-5-derived herpesvirus thymidine kinase)

(2) Test Method

Equal amounts (3.5 μL) of a virus solution and a reagent were mixed, followed by reaction at room temperature for 3 minutes. A 10-fold dilution series was formed using a diluent and inoculated in FL cells on a cover slip to measure viral infectivity.

Diluent: Eagle's minimum essential medium, penicillin G, streptomycin (serum-free)

(3) Method for Measuring Viral Infectivity

Monolayer FL cells (cell line contaminated with HeLa cells (derived from human cervical cancer epithelial cells)) on the cover slip (9×28 mm) were washed with PBS one time and then infected with a 50 μL of virus solution. After adsorption for 1 hour, the cells were washed with PBS one time, and then a maintenance solution (the same as the diluent) was added, followed by culture.

Two days after, fluorescent staining was performed with anti-adenovirus antibody (monoclonal antibody: Chemicon MAB805) and Alexa Fluor 488-labeled anti-mouse IgG antibody (SantaCruz Biotechnology), and positive cells were counted in a field of view under a fluorescent microscope (400 times) (average of 20 fields of view was calculated). The number of positive cells per cover slip was calculated on the basis of the area of the field of view, and further infectivity per mL of virus solution was calculated (unit: CIU (cell infecting units)/ml; Kiyotani et al., Virology 177:65-74, 1990).

Figure 2:
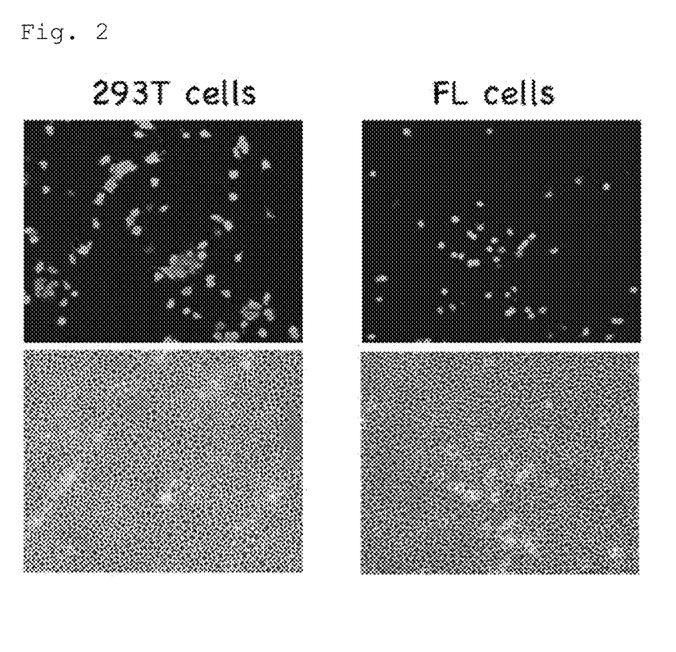
FIG. 2 is a fluorescent staining photograph of adenovirus-infected cells with anti-adenovirus antibody in Example 3.

The adenovirus used synthesizes virus proteins in the FL cells after first infection, but does not produce virus progeny and not spread to neighbor cells and surrounding cells. Therefore, each positive cell corresponds to at least one infectious virus. Thus, the infectivity of the initial virus solution can be measured. FIG. 2 shows an actual fluorescent microscope image. This virus is capable of multistage proliferation in 293T cells, and spread to neighbor cells can be observed.

(4) Experiment Result

Figure 3:
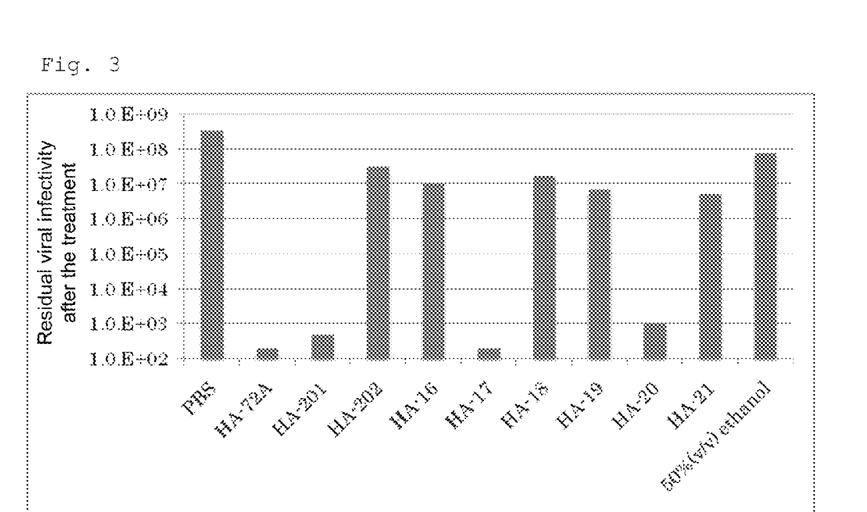
FIG. 3 is a graph showing the antiviral effect of each of reagents on adenovirus in Example 3.

The antiviral action of each reagent was as shown in Table 5 and FIG. 3.

TABLE 5

| Reagent | Residual infectivity after treatment | Infectivity ratio (to PBS) | Effect (times) (to PBS) |
|---|---|---|---|
| PBS | 3.3E+08 | 1 | 1 |
| HA-72A persimmon juice FD powder | 2.0E+02 | 0.0000006 | 1662498 |
| 50% (v/v) ethanol | 7.7E+07 | 0.2 | 4 |
| HA-201 persimmon juice FD powder | 5.0E+02 | 0.000002 | 664999 |
| HA-202 citric acid | 3.1E+07 | 0.09 | 11 |
| HA-16 pentagalloyl glucose | 9.9E+06 | 0.03 | 33 |
| HA-17 wattle tannin | 2.0E+02 | 0.0000006 | 1662498 |
| HA-18 coffee tannin | 1.7E+07 | 0.05 | 19 |
| HA-19 propyl gallate | 7.2E+06 | 0.02 | 46 |
| HA-20 green tea tannin | 1.0E+03 | 0.000003 | 332500 |
| HA-21 pyrogallol | 5.3E+06 | 0.02 | 63 |

HA-72A has high inactivation activity for adenovirus. Although 50% ethanol and citric acid+50% ethanol (HA-202) have no inactivation ability, 1% persimmon extract+50% ethanol (HA-201) suppresses adenovirus infectivity. Thus it is thought that persimmon extract mainly contributes to antiviral activity for adenovirus. Other reagents, such as tannic acid and catechin, have the same high inactivation activity for adenovirus.

In this experiment, gene defective nonproliferating adenovirus was used in place of adenovirus, but it is supposed that although the gene is partially defective, the particle structure and the adsorption and penetration process of viruses are the same as general viruses. Therefore, the results of the experiment are considered to apply to usual adenovirus.

The results shown in Table 5 and FIG. 3 indicate that persimmon extract, tannic acid, and catechin have remarked anti-adenovirus effect.

Example 4

Verification of Effect on Feline Calicivirus (1) Test Virus

Feline calicivirus (non-enveloped virus, 2 passages in CRFK cells, distributed from National Institute of Health Sciences, previous isolation and passage history unknown)

(2) Cells

CRFK cells: cultured cells derived from a cat kidney, distributed from National Institute of Health Sciences (supposed to be the same as ATCCCCL-94).

(3) Method for Measuring Viral Infectivity

To eliminate the influence of serum contained in the original virus, a virus solution was previously 5 times diluted with a diluent (Eagle's minimum essential medium, penicillin G, streptomycin). Equal amounts (35 μL) of the diluted virus solution and each reagent were mixed and allowed to react at room temperature for 3 minutes. Then, a ten-fold dilution series was prepared using the diluent.

Monolayer CRFK cells on a 96-well plate were washed with PBS one time and then the diluted virus solution was inoculated (50 μl/well). After incubation with a $CO_2$ incubator for adsorption and penetration of the virus for 1 hour, the cells were washed with PBS one time, and then a maintenance solution (the same as the diluent) was added (100 μL/well), followed by culture. Three days after, the cells were fixed and stained after extension of CPE, and a 50% infectious dose (unit: 50% tissue culture infectious dose [TCID50]) was calculated using a Behrens-Kaerber method to measure viral infectivity.

Figure 4:
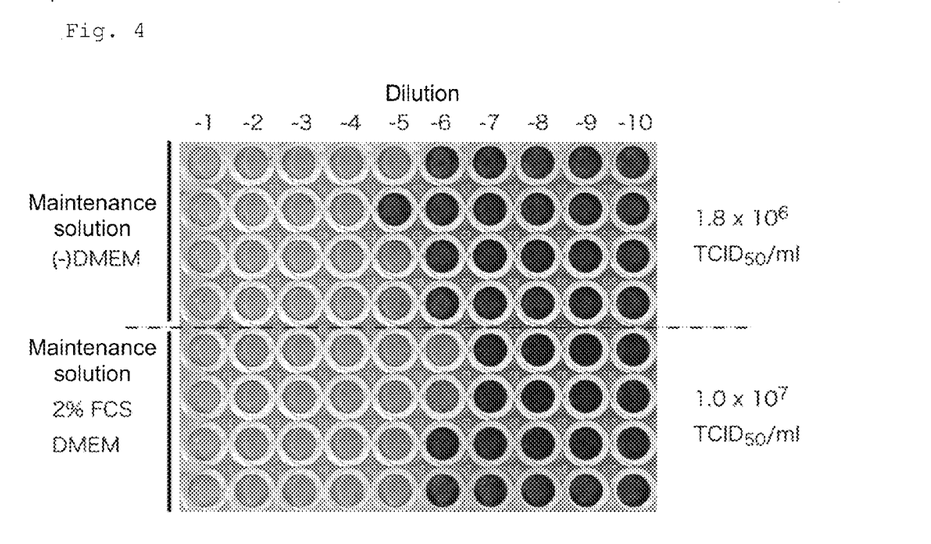
FIG. 4 is a drawing showing an example of a plate after fixing and staining in a feline calicivirus test in Example 4.

FIG. 4 shows an example of a plate after fixing and staining, and the calculated infectivity is described below (in a preliminary experiment, the effect was investigated by adding serum to the maintenance solution).

(4) Experiment Result

Figure 5:
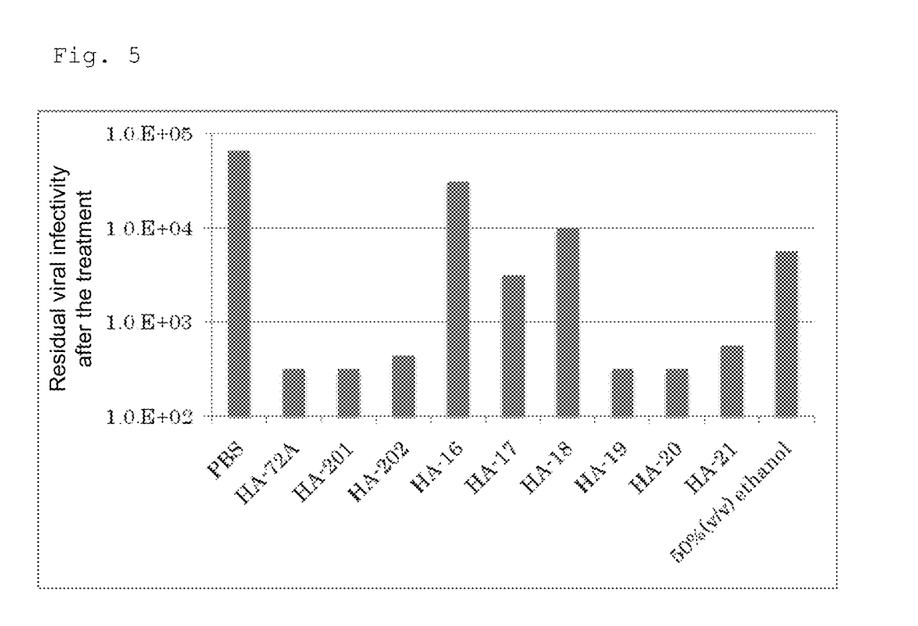
FIG. 5 is a graph showing the antiviral effect of each of reagents on feline calicivirus in Example 4.

The antiviral action of each reagent was as shown in Table 6 and FIG. 5.

TABLE 6

| Reagent | Infectivity (TCID50/ml) | Infectivity ratio (to PBS) | Effect (times) (to PBS) |
|---|---|---|---|
| PBS | 1.5E+07 | 1 | 1 |
| HA-72A persimmon juice FD powder | 3.2E+02 | 0.005 | 208 |
| HA-201 persimmon juice FD powder | 4.4E+02 | 0.005 | 208 |
| HA-202 citric acid | 6.6E+07 | 0.007 | 150 |
| HA-16 pentagalloyl glucose | 7.8E+06 | 0.5 | 2 |
| HA-17 wattle tannin | 3.2E+06 | 0.05 | 21 |
| HA-18 coffee tannin | 3.2E+07 | 0.2 | 7 |
| HA-19 propyl gallate | 3.7E+07 | 0.005 | 208 |
| HA-20 green tea tannin | 1.7E+07 | 0.005 | 208 |
| HA-21 pyrogallol | 7.8E+07 | 0.009 | 117 |
| 50% (v/v) ethanol | 3.2E+07 | 0.09 | 12 |

In this experiment, the inoculation time of the virus solution was only 1 hour in order to minimize the toxic influence of a medicine on cells, but the cells were damaged by the medicine at $10^{-1}$ dilution. Assuming that a damage at $10^{-1}$ dilution is due to viral infection, the damage corresponds to an infectivity of 3.2×101 TCID50/ml. It is impossible to determine whether results lower than this value are due to the medicine or the virus, and thus the experiment is meaningless. Therefore, a graph was formed using this value as a lower limit.

HA-72A and HA-201 (persimmon extract) showed high suppression of infectivity, and thus it was confirmed that persimmon tannin has an inactivation effect on feline calicivirus. On the other hand, a viral inhibitory effect was also observed with HA-202 (citric acid), HA-19 (propyl gallate), HA-20 (green tea tannin), and HA-21 (pyrogallol).

The virus was inactivated with HA-202 (citric acid), while the virus was not inactivated with HA-16. Also, the experiment was repeated to confirm reproducibility. As a result of measurement of pH of the reagents, a small difference was found between pH 4.0 of HA-202 and pH 4.20 of HA-16 (Table 7).

TABLE 7

| | pH meter (Beckmann) | pH test paper (1 pH increments) |
|---|---|---|
| HA-72A persimmon juice FD powder | 4.05 | 4 |
| HA-201 persimmon juice FD powder | 5.41 | 5 |
| HA-202 citric acid | 4.00 | 4 |
| HA-16 pentagalloyl glucose | 4.20 | 4 |

Such a difference in pH is possibly significant for inactivation of feline calicivirus. It is generally considered that feline calicivirus is a respiratory virus and has high sensitivity to an acid.

Example 5

Verification of Effect on Rotavirus (1) Virus Used

Rotavirus Wa Strain

This strain was distributed from Okayama Prefectural Institute for Environmental Science and Public Health by Mitsutaka KUZUYA. In Okayama Prefectural Institute for Environmental Science and Public Health, a strain distributed from Mitsuaki OSETO, Ehime Prefectural Institute of Public Health Environmental Science was subjected to 88 passages. Rotavirus is a non-enveloped virus (diameter 60 to 80 nm) belonging to the genus Rotavirus of the family Reoviridae and having a gene consisting of segmented double-stranded. RNA and causes acute gastroenteritis. In particular, rotavirus causes winter diarrhea in infancy (referred to as "white diarrhea" because feces is like a white-rice washing liquid).

(2) Cells

MA104 cells (derived from African green monkey fetal kidneys, epithelioid) were distributed from Mitsutaka KUZUYA, Okayama Prefectural Institute for Environmental Science and Public Health, which had been subjected to 55 passages there. The cells were cultured in Eagle's minimum essential medium (MEM) containing 10% fetal bovine serum (FBS).

(3) Method for Measuring Viral Infectivity

Equal amounts (35 µL) of a virus solution and a reagent were mixed, followed by reaction at room temperature for 3 minutes. A 10-fold dilution series was formed using a diluent (MEM) and the MA104 cells on a cover slip (9×28 mm) were infected with 50 µL of the virus solution. After adsorption for 1 hour, the cells were washed with PBS one time and a growth medium (10% PBS-MEM) was added, followed by culture.

One day after, fluorescent staining was performed with anti-rotavirus antibody (monoclonal antibody: Abgene REMEI-1) and Alexa Fluor 488-labeled anti-mouse IgG antibody (SantaCruz Biotechnology), and positive cells were counted in a field of view under a fluorescent microscope (400 times) (average area of 20 fields of view). The number of positive cells per cover slip was calculated on the basis of the area of the field of view, and further infectivity per mL of virus solution was calculated (unit: CIU (cell infecting units)/ml; Kiyotani et al., Virology 177:65-74, 1990). When the number of positive cells was small, the positive cells were measured by observing the whole of the cover slip.

Figure 6:
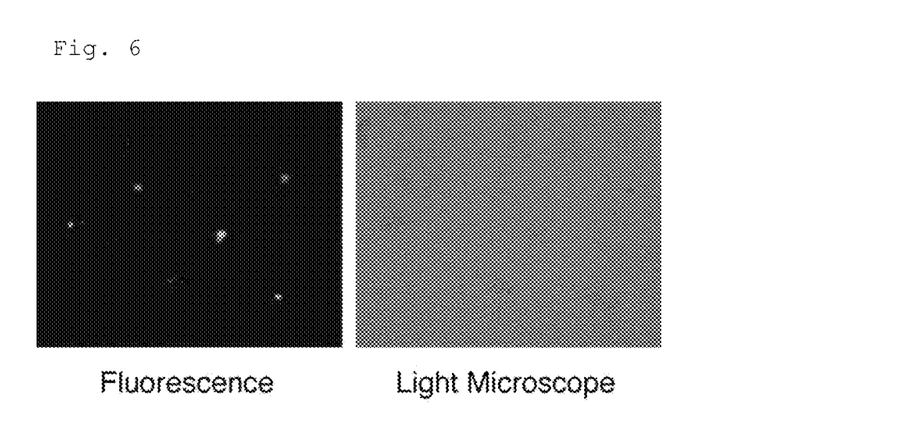
FIG. 6 is a fluorescent staining photograph of rotavirus-infected cells with anti-rotavirus antibody in Example 5.

Rotavirus requires trypsin for multistage proliferation. In this measurement, trypsin was not added, and thus viruses produced from the first infected cell did not infect neighbor cells. Therefore, each positive cell corresponds to almost one infectious virus. Thus, the infectivity of the initial virus solution can be measured. FIG. 6 shows an actual fluorescent microscope image.

(4) Experiment Result

The antiviral action of each reagent was as shown in Table 8. Rotavirus was inactivated with any one of persimmon extract, citric acid, pentagalloyl glucose, wattle tannin, coffee tannin, propyl gallate, green tea tannin, and pyrogallol (each mixed with 50% ethanol). In addition, imperfect inactivation was exhibited only with 50% (v/v) ethanol, but substantially perfect inactivation was achieved by increasing the ethanol concentration to 80% (v/v).

TABLE 8

| Reagent | Residual infectivity after treatment | Infectivity ratio (to PBS) |
|---|---|---|
| PBS | 1.1E+07 | 1 |
| HA-72A persimmon juice FD powder | 0 | 0 |
| 50% (v/v) ethanol | 6.2E+05 | 0.06 |
| 80% (v/v) ethanol | 0 | 0 |
| HA-201 persimmon juice FD powder | 8.0E+01 | 0.000007 |
| HA-202 citric acid | 0 | 0 |
| HA-16 pentagalloyl glucose | 8.0E+01 | 0.000007 |
| HA-17 wattle tannin | 4.0E+01 | 0.000004 |
| HA-18 coffee tannin | 0 | 0 |
| HA-19 propyl gallate | 0 | 0 |
| HA-20 green tea tannin | 0 | 0 |
| HA-21 pyrogallol | 0 | 0 |

The antiviral effects of each of the reagents on Coxsackie virus, adenovirus, feline calicivirus, and rotavirus in Examples 2 to 5 described above are summarized in the table below.

TABLE 9

| Reagent | pH | Coxsackie virus | Feline calicivirus | Adenovirus | Rotavirus |
|---|---|---|---|---|---|
| HA-72A persimmon juice FD powder | 4.05 | ○ | ○ | ○ | ○ |
| HA-201 persimmon juice FD powder | 5.41 | ○ | ○ | ○ | ○ |
| HA-202 citric acid | 4.00 | X | ○ | X | ○ |
| 50% (v/v) ethanol | 5.09 | X | X | X | X |
| HA-16 pentagalloyl glucose | 4.20 | X | X | X | ○ |
| HA-17 wattle tannin | | X | X | ○ | ○ |
| HA-18 coffee tannin | | X | X | X | ○ |
| HA-19 propyl gallate | | X | ○ | X | ○ |
| HA-20 green tea tannin | | X | ○ | ○ | ○ |
| HA-21 pyrogallol | | X | ○ | X | ○ |

○: Having antiviral effect,
X: Having no antiviral effect

The invention claimed is:

1. A method for inhibiting a non-enveloped virus in vitro, comprising contacting said virus with a composition comprising an effective amount of a tannin-containing extract from an astringent fruit of *Diospyros kaki*, wherein the non-enveloped virus is selected from the group consisting of Coxsackie virus B5, Adenovirus, Feline calicivirus and Rotavirus Wa strain, and wherein the extract is prepared by the following method:
a) removing calyx from an astringent fruit of *Diospoyros kaki* and sterilizing the calyx-removed fruit with sodium hypochlorite (NaClO),
b) treating the NaClO-sterilized fruit of part (a) with Vitamin C and crushing the fruit,
c) passing the crushed fruit through a 200 mesh sieve, centrifuging to obtain a juice, sterilizing the juice at a temperature from 120° C. to 130° C. for 7 to 10 seconds and
d) freeze drying the sterilized liquid produced in step (c) to produce said *Diospyros kaki* extract.

2. The method according to claim 1, wherein the composition further comprises at least one compound selected from the group consisting of a catechin, wattle tannin, pentagalloyl glucose, coffee tannin, an alkyl gallate, pyrogallol and an organic acid and/or a salt thereof, whereby the alkyl gallate, organic acid and organic acid salt are not endogenous to the *Diospyros kaki* extract.

3. The method according to claim 1, wherein the composition is an antiviral alcohol preparation further comprising an alcohol.

4. The method according to claim 1, wherein the composition is an antiviral washing composition further comprising a surfactant.

5. The method according to claim 1, wherein the composition is an antiviral disinfectant composition further comprising an antimicrobial agent other than ethanol, an organic acid and a salt thereof.

6. The method according to claim 1, wherein the composition comprises the *Diospyros kaki* extract at a ratio of 0.01% to 5% by weight (in terms of solid content) based on the total composition.

7. The method according to claim 1, wherein the composition further comprises vitamin C.

8. The method according to claim 1, wherein the composition comprises an organic acid and/or a salt thereof, which is not endogenous to the *Diospyros kaki* extract.

* * * * *

UNITED STATES PATENT AND TRADEMARK OFFICE
CERTIFICATE OF CORRECTION

PATENT NO. : 9,445,605 B2
APPLICATION NO. : 13/939692
DATED : September 20, 2016
INVENTOR(S) : Tadashi Shimamoto et al.

It is certified that error appears in the above-identified patent and that said Letters Patent is hereby corrected as shown below:

Title Page, Column 1, Related U.S. Application Data, Lines 2-3, delete "Mar. 31, 2006" and insert -- Mar. 31, 2009 --

In the Claims

Column 26, Line 52, Claim 1, delete "Diospoyros" and insert -- Diospyros --

Signed and Sealed this
Twenty-ninth Day of November, 2016

Michelle K. Lee
*Director of the United States Patent and Trademark Office*